US008137657B2

(12) United States Patent
Staniforth (10) Patent No.: US 8,137,657 B2
(45) **Date of Patent: *Mar. 20, 2012**

(54) CARRIER PARTICLES FOR USE IN DRY POWDER INHALERS

(75) Inventor: John Nicholas Staniforth, Bath (GB)

(73) Assignee: Vectura Limited, Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/439,820

(22) Filed: May 16, 2003

(65) Prior Publication Data

US 2003/0202944 A1 Oct. 30, 2003

Related U.S. Application Data

(63) Continuation of application No. 09/841,055, filed on Apr. 23, 2001, now Pat. No. 6,582,678, which is a continuation of application No. 08/633,814, filed as application No. PCT/GB94/02353 on Oct. 26, 1994, now Pat. No. 6,221,338.

(30) Foreign Application Priority Data

Oct. 26, 1993 (GB) .................................. 9322014.3

(51) Int. Cl.
*A61K 9/14* (2006.01)
*A61K 9/12* (2006.01)
*A61K 9/00* (2006.01)

(52) U.S. Cl. ............. 424/46; 424/489; 424/45; 424/400

(58) Field of Classification Search .................... 424/45, 424/400, 434, 490, 60, 452, 423, 489, 46
See application file for complete search history.

(56) References Cited

U.S. PATENT DOCUMENTS

| | | | | | |
|---|---|---|---|---|---|
| 2,533,065 | A | | 12/1950 | Taplin et al. | |
| 3,809,294 | A | * | 5/1974 | Torgeson | 222/182 |
| 3,897,779 | A | * | 8/1975 | Hansen | 128/203.15 |
| 3,956,330 | A | * | 5/1976 | Corey et al. | 544/390 |
| 3,957,965 | A | * | 5/1976 | Hartley et al. | 424/452 |
| 4,161,516 | A | | 7/1979 | Bell | |
| 4,199,578 | A | * | 4/1980 | Stevenson | 514/171 |
| 4,379,171 | A | * | 4/1983 | Furda et al. | 426/291 |
| 4,847,277 | A | * | 7/1989 | Gould | 514/382 |
| 4,866,051 | A | * | 9/1989 | Hunt et al. | 514/180 |
| 5,642,728 | A | | 7/1997 | Andersson et al. | |

(Continued)

FOREIGN PATENT DOCUMENTS

AU 30854/92 7/1994

(Continued)

OTHER PUBLICATIONS

Second Collegiate Edition, The American Heritage Dictionary, 1982, p. 797.*

(Continued)

*Primary Examiner* — Blessing M Fubara
(74) *Attorney, Agent, or Firm* — Merchant & Gould P.C.

(57) ABSTRACT

In a method of producing particles suitable for use as carrier particles in dry powder inhalers, particles (1) of a size suitable for use as carrier particles in dry powder inhalers are treated so as to dislodge small grains from the surface of the particles, without substantially changing the size of the particles during the treatment. The treatment gives improved efficiency of redispersion of active particles from the surfaces of carrier particles.

20 Claims, 2 Drawing Sheets

U.S. PATENT DOCUMENTS

| | | | | |
|---|---|---|---|---|
| 6,153,224 | A * | 11/2000 | Staniforth | 424/490 |
| 6,221,338 | B1 * | 4/2001 | Staniforth | 424/45 |
| 6,521,260 | B1 * | 2/2003 | Staniforth | 424/490 |
| 6,582,678 | B2 * | 6/2003 | Staniforth | 424/45 |
| 7,011,818 | B2 * | 3/2006 | Staniforth | 424/45 |

FOREIGN PATENT DOCUMENTS

| | | |
|---|---|---|
| EP | 0 124 493 | 4/1984 |
| EP | 0 187 433 | 1/1985 |
| EP | 0 239 798 | 2/1987 |
| GB | 786499 | 10/1954 |
| GB | 905723 | 3/1961 |
| GB | 1132583 | 12/1965 |
| GB | 1230087 | 7/1968 |
| GB | 1242211 | 7/1968 |
| GB | 1242212 | 7/1968 |
| GB | 1310527 | 5/1970 |
| GB | 1381872 | 6/1972 |
| GB | 1410588 | 7/1972 |
| GB | 2 240 337 | 1/1991 |
| GB | 2 269 992 | 3/1994 |
| WO | 87/05213 | 9/1987 |
| WO | 91/11173 | 8/1991 |
| WO | 91/14422 | 10/1991 |
| WO | 92/08447 | 5/1992 |
| WO | 93/11746 | 6/1993 |
| WO | 94/04133 | 3/1994 |
| WO | 94/13271 | 6/1994 |
| WO | 95/00127 | 1/1995 |
| WO | 95/00128 | 1/1995 |
| WO | 95/11666 | 5/1995 |
| WO | WO 95/11666 * | 5/1995 |
| WO | 96/23405 | 8/1996 |
| ZA | 94/0155 | 7/1995 |

OTHER PUBLICATIONS

Eighteenth edition, Remington's Pharmaceutical Sciences, 1990, p. 1618.*

Gennaro. A.R., (1985)Remington's, Pharmaceutical Sciences, Mack Publishing Company, PA, pp. 1585-1587.

Wong, et al., "The effect of the Shape of Fine Particles on the Inhalation Properties of Powder Mixtures", 1989, *J. Pharm Pharmacol, 41* Suppl., p. 24P.

Ward, et al., "A clinically relevant modification on existing inhaler therapy", *Respiratory Medicine 86*, 1992, pp. 237-241.

Ganderton, D., "The Gernearion of Respirable Clouds Form Coarse Powder Aggregates", *Journal of Biopharmaceutical Sciences*, vol. 3, Issues 1 & 2, Mar. & Jun. 1992.

Kassem, N., "Generation of Deeply Inspriable Clouds From Dry Powder Mixtures", A Thesis Submitted in Partial Fulfillment of Requirements for the Award of the Degree of Doctor of Philosophy 275 pages total (1990).

Harris et al., "Powder Dispersibility Testing: The Importance of Optimising Formulation to Device", *Proceedings of Drug Delivery to the Lungs XV*, Dec. 9-10, 2004, London, UK.

* cited by examiner

Fig.3 ly used type is a metered dose inhaler (MDI)
CARRIER PARTICLES FOR USE IN DRY POWDER INHALERS This invention relates to carrier particles for use in dry powder inhalers. More particularly the invention relates to a method of producing such particles, to a dry powder incorporating the particles and to the particles themselves.

Inhalers are well known devices for administering pharmaceutical products to the respiratory tract by inhalation. Inhalers are widely used particularly in the treatment of diseases of the respiratory tract.

There are a number of types of inhaler currently available. The most widely used type is a metered dose inhaler (MDI) which uses a propellant to expel droplets containing the pharmaceutical product to the respiratory tract. Those devices are disadvantageous on environmental grounds as they use CFC propellants.

An alternative device to the MDI is the dry powder inhaler. The delivery of dry powder particles of pharmaceutical products to the respiratory tract presents certain problems. The inhaler should deliver the maximum possible proportion of the active particles expelled to the lungs, including a significant proportion to the lower lung, preferably at the low inhalation capabilities to which some patients, especially asthmatics, are limited. It has been found, however, that, when currently available dry powder inhaler devices are used, in many cases only about 10% of the active particles that leave the device on inhalation are deposited in the lower lung. More efficient dry powder inhalers would give clinical benefits.

The type of dry powder inhaler used is of significant importance to the efficiency of delivery of the active particles to the respiratory tract. Also, the physical properties of the active particles used affect both the efficiency and reproducibility of delivery of the active particles and the site of deposition in the respiratory tract.

On exit from the inhaler device, the active particles should form a physically and chemically stable aerocolloid which remains in suspension until it reaches an alveolar or other absorption site preferably in the lungs. Once at the absorption site, the active particle should be capable of efficient collection by the pulmonary mucosa with no active particles being exhaled from the absorption site.

The size of the active particles is particularly important. For effective delivery of active particles deep into the lungs, the active particles should be small, with an equivalent aerodynamic diameter substantially in the range of 1 to 5 µm, approximately spherical and monodispersed in the respiratory tract. Small particles are, however, thermodynamically unstable due to their high surface area to volume ratio, which provides significant excess surface free energy and encourages particles to agglomerate. In the inhaler, agglomeration of small particles and adherence of particles to the walls of the inhaler are problems that result in the active particles leaving the inhaler as large agglomerates or being unable to leave the inhaler and remaining adhered to the interior of the inhaler.

The uncertainty as to the extent of agglomeration of the particles between each actuation of the inhaler and also between different inhalers and different batches of particles, leads to poor dose reproducibility. It has been found that powders are reproducibly fluidisable, and therefore reliably removable from an inhaler device, when the particles have a diameter greater than 90 µm.

To give the most effective dry powder aerosol, therefore, the particles should be large while in the inhaler, but small when in the respiratory tract.

In an attempt to achieve that situation, one type of dry powder for use in dry powder inhalers may include carrier particles to which the fine active particles adhere whilst in the inhaler device, but which are dispersed from the surfaces of the carrier particles on inhalation into the respiratory tract to give a fine suspension. The carrier particles are often large particles greater than 90 µm in diameter to give good flow properties as indicated above. Small particles with a diameter of less than 10 µm may become coated on the wall of the delivery device and have poor flow and entrainment properties leading to poor dose uniformity.

The increased efficiency of redispersion of the fine active particles from the agglomerates or from the surfaces of carrier particles during inhalation is regarded as a critical step in improving the efficiency of the dry powder inhalers.

It is known that the surface properties of a carrier particle are important. The shape and texture of the carrier particle should be such as to give sufficient adhesion force to hold the active particles to the surface of the carrier particle during fabrication of the dry powder and in the delivery device before use, but that force of adhesion should be low enough to allow the dispersion of the active particles in the respiratory tract.

It is an object of the invention to provide a method of producing carrier particles for use in dry powder inhalers and to provide carrier particles that overcome or mitigate the problems referred to above.

According to the invention there is provided a method of producing particles suitable for use as carrier particles in dry powder inhalers, the method including the step of treating particles of a size suitable for use as carrier particles in dry powder inhalers to dislodge small grains from the surfaces of the particles, without substantially changing the size of the particles during the treatment.

The surface of the carrier particle is not smooth but has asperities and clefts in the surface. The site of a cleft or an asperity is often found to be an area of high surface energy. The active particles are preferentially attracted to and adhere most strongly to those high energy sites causing uneven and reduced deposition of the active particles on the carrier surface. If an active particle adheres to a high energy site, it is subjected to a greater adhesion force than a particle at lower energy sites on the carrier particle and will therefore be less likely to be able to leave the surface of the carrier particle and be dispersed in the respiratory tract. During the treatment asperities are removed as small grains, thus removing active sites associated with the asperities.

Advantageously, the small grains become reattached to the surfaces of the particles. The object of treating the carrier particles is to reduce the number of high energy sites on the carrier particle surfaces, thus allowing an even deposition of active particles adhered on the surface with a force of adhesion such that dispersion of the active particles during inhalation is efficient. While removing asperities as small grains removes those high energy sites associated with the asperities, the surfaces of the carrier particle have other high energy sites, for example at the site of clefts, which sites are not necessarily removed when the apserities are removed. It would therefore be highly advantageous to decrease the number of those high energy sites.

The grains removed from the surface are small and thermodynamically unstable and are attracted to and adhere to the high energy sites on the surface of the carrier particle. On introduction of the active particles, many of the high energy sites are already occupied, and the active particles therefore occupy the lower energy sites on the carrier particle surfaces. That results in the easier and more efficient release of the active particles in the airstream created on inhalation, thereby giving increased deposition of the active particles in the lungs.

Advantageously, the treatment step is a milling step. The milling process causes asperities on the surfaces of the carrier particles to be dislodged as small grains. Many of those small grains become reattached to the surfaces of the carrier particles at areas of high energy.

Preferably, the milling step is performed in a ball mill. Preferably, the carrier particles are milled using plastics or steel balls. Balls made of plastics material give less aggressive milling, whilst steel balls confer more efficient surface smoothing. Advantageously, the mill is rotated at a speed of less than about 60 revolutions per minute, more advantageously at a speed of less than about 20 revolutions per minute, and most preferably at a speed of about six revolutions per minute. That is a slow speed for ball milling and results in the gentle removal of grains from the surfaces of the particles and little fracture of particles. Fracture of the particles, which occurs with aggressive milling conditions, for example at higher milling speeds such as 60 revolutions per minute and/or long milling times, may result in agglomerates of fractured particles of carrier material. The use of agglomerates of particles as carrier particles has been found to lead to good deposition of active particles in the lower lung.

Advantageously, the particles are milled for at least one hour, preferably the particles are milled for about six hours. That time has been found to be suitable when milling with balls made from plastics material. When using denser balls, shorter milling times may be used. Alternatively, a different milling technique may be used, for example using a re-circulated low fluid energy mill, or other method that results in the removal of grains from the surfaces of the particles e.g. sieving.

The carrier particles may include may acceptable pharmacologically inert material or combination of materials. Advantageously, the carrier particles are crystalline sugar particles. Preferably, the carrier particles are lactose particles.

Advantageously, the diameter of the carrier particles lies between 50 µm and 1000 µm. Preferably, the diameter of the carrier particles is less than 355 µm and lies between 60 µm and 250 µm, more preferably 90 µm and 250 µm. The relatively large diameter of the carrier particle improves the opportunity for active particles to become attached to carrier particles which is controlled by the above technique to provide good flow and entrainment characteristics and improved release of the active particles in the airways to increase deposition of the active particles in the lower lung.

The size of the carrier particles is an important factor in the efficiency of the inhaler, and an optimum, or near optimum, range of size of carrier particles is preferably selected. The optimum range of size of carrier particles may differ according to the inhaler device and active particles used. Thus, the method preferably includes the step of selecting an advantageous range of size of carrier particles prior to the treatment step. That step of selecting an advantageous range of size may be a sieving step.

According to the invention, there is also provided a method of producing a dry powder for use in dry powder inhalers, the method including the steps of treating carrier particles to dislodge small grains from the surfaces of the carrier particles without substantially changing the size of the carrier particles during the treatment step, and mixing the treated carrier particles with active particles such that active particles adhere to the surfaces of carrier particles.

Advantageously, the small grains become reattached to the surfaces of the carrier particles.

Advantageously, the method includes the steps of treating carrier particles according to the present invention and mixing the treated carrier particles with the active particles such that active particles adhere to the surfaces of carrier particles. The treatment of the carrier particles may be carried out before the active particles are added, but it may also be carried out in the presence of the active particles.

Advantageously, the carrier particles and the active particles are mixed in a container made from a plastics material. That has been found to give an unstable mixture of salbutamol and lactose and thus increases the deposition of salbutamol in the lungs. A container of different material may be used when using a mixture containing a different type of active particles.

Advantageously, the carrier particles and the active particles are mixed for at least five minutes. Preferably, the carrier particles and the active particles are mixed for about thirty minutes. The mixing should be for a time sufficient to give a homogeneous mixture of the active particles and the carrier particles, during mixing, rearrangement of the sites of particles may also occur, even when the system is homogeneous.

Advantageously, the mixing is interrupted and the mixture of carrier particles and active particles is sieved. The sieving of the mixture reduces the number of large agglomerates present. Preferably, the sieve mesh size is about 250 µm.

The ratio in which the carrier particles and active particles are mixed is dependent on the inhaler device and the active particles used. For the example given below, a ratio of 125 to 1 by weight is preferably used.

Advantageously, the diameter of the active particles is between 0.1 µm and 3 µm such that the particles give a good suspension on redispersion from the carrier particles and are delivered deep into the respiratory tract.

The active particles may include a $\beta_2$-agonist which may be terbutaline, a salt of terbutaline or a combination thereof or may be salbutamol, a salt of salbutamol or a combination thereof. Salbutamol and its salts are widely used in the treatment of respiratory disease. The active particles may be particles of salbutamol sulphate.

The active particles may include a steroid, which may be beclomethasone dipropionate. The active principle may include a cromone which may be sodium cromoglycate. The active principle may include a leukotriene receptor antagonist.

According to the invention, there are also provided particles suitable for use as carrier particles in a dry powder inhaler, the particles consisting of small grains and large particles to the surfaces of which the small grains are attached.

Preferably, the small grains have a diameter between 1 µm and 5 µm and, preferably, the large particles have a diameter between 50 µm and 1000 µm.

Preferably, the large particles are particles of lactose.

According to the invention, there are also provided particles suitable for use as carrier particles in a dry powder inhaler wherein the particles are made by a method according to the invention.

According to the invention there is further provided a dry powder suitable for use in a dry powder inhaler including carrier particles according to the invention and active particles, wherein active parties adhere to the surfaces of carrier particles.

The carrier particles usually consist of a particulate crystalline sugar. Lactose particles are often used as carrier particles.

The active particles referred to throughout the specification will be particles of one or a mixture of pharmaceutical products. Those pharmaceutical products include those products which are usually administered orally by inhalation for the treatment of disease such as respiratory disease eg. β-agonists, salbutamol and its salts. Other pharmaceutical products which could be administered using a dry powder inhaler include peptides and polypeptides, such as insulin. In addition the method could find use in nasal delivery.

According to a further aspect of the invention, there is provided a method of producing particles including the step of treating large particles such that small grains adhere to the surfaces of the large particles.

As indicated above, the surfaces of the large particles are not completely smooth even following treatment such as milling but have asperities and clefts. As a result, the surfaces have areas of high surface energy to which active particles are preferentially attached. An active particle at a high energy site is less likely to be able to leave the surface and be dispersed in the respiratory tract than an active particle at a site of lower surface energy. During the treatment of the large particles, the small grains are attracted to and adhere to high energy sites on the surface of the large particles. On the introduction of the active particles, many of the high energy sites are already occupied, and the active particles therefore occupy the lower energy sites on the carrier particle surfaces. That results in the easier and more efficient release of the active particles in the airstream created on inhalation, thereby giving increased deposition of the active particles in the lungs.

Advantageously the step of treating large particles such that small grains adhere to the surfaces of the large particles is a mixing step. Small grains, or agglomerates of small grains, may be introduced to a sample of large particles which may have been treated to dislodge small grains from the surfaces of the particles and the mixture blended for several hours to allow the small grains to become attached to the surfaces of the large particles.

The small grains added to the large particles are preferably the product of milling large particles. If the large particles are subjected to aggressive milling, for example at high milling speed, small grains are produced. Those small grains may form larger agglomerates.

Advantageously, the large particles and small grains are mixed in a ratio by weight of at least one part of large particles to each part of stall grains. For example, the proportion of small grains may be between 10 and 30 per cent, especially of the order of 20 per cent by weight based on the combined weight of the small grains and the large particles. It has been found to be highly advantageous for the surfaces of the large particles to become saturated with small grains. Some of the small grains may act as carrier particles for active particles, by leaving the surfaces of the large particles with active particles attached to their surfaces. The dimensions of the combined active particle and small grain are generally still within the optimum values for good deposition in the lower lung. It is believed that active particles which adhere to the small grains on the large particles, are preferentially released from the surface of the large particles.

Embodiments of the invention will now be described by way of example with reference to the accompanying drawings, of which:

FIGS. 1*a* to *c* show the effect of a milling treatment on the surface of a particle, FIG. 2 is a perspective view of a dry powder inhaler, FIG. 3 is a sectional diagram of a twin stage impinger.

The following Examples illustrate the invention.

EXAMPLE 1

Carrier particles were prepared by the following method. Meggle lactose EP D30 (an α lactose monohydrate: pure crystalline milk sugar) was used. Lactose EP D30 has a useful starting particle size range and acceptable flow properties.

(a) The lactose was sieved by the following method conforming to British Standard No. 410 to give samples having particles with a range of diameter from 90 to 125 μm. Samples of 30 g of Lactose EP D30 were sieved mechanically for 20 minutes using a stack of woven wire stainless steel sieves of mesh aperture diameters 90 μm, 125 μm and 180 μm. The mesh was vibrated at high speed to reduce the binding of lactose particles to the mesh of the sieve. After ten minutes of the sieving process, the sieving was stopped and each of the sieves was dismantled individually and the powder on the sieve was removed, the sieve brushed and the powder replaced in the sieve from which it was removed. The sieve stack was then reassembled and the sieving resumed. This was done in an attempt to improve the efficiency of the sieving process.

50 g samples of the lactose EP D30 were taken from the particles that had passed through the 125 μm mesh sieve but had remained on the 90 μm sieve. Those particles could be considered to have a diameter between 90 μm and 125 μm.

(b) The samples obtained in step (a) above were milled in a porcelain ball mill (manufactured by Pascal Engineering Company). Plastics grinding balls having an approximate diameter of 10 mm were used and the mill which had a diameter of approximately 150 mm was revolved at a slow speed of 6 revolutions per minute for six hours. During the milling process, the mill was periodically stopped and any powder adhered to the mill wall or to the plastics grinding balls, was scraped free.

(c) Small samples of the milled lactose particles were mounted for scanning electron microscope (SEM) analysis and were sputtered with gold. The SEM analysis showed the extent of grinding of the lactose particles and the alteration of the surfaces of the lactose particles.

FIG. 1*a* shows a representation of an untreated particle 1 having asperities 2 and clefts 3. FIG. 1*b* shows the effect of a milling treatment on the particle of FIG. 1*a*. Shaded areas 4 represent the sections removed from the surface of the particle as small grains during the milling.

In FIG. 1*c* small grains 5 have become reattached to the surface of the particle, mostly at active sites on the surface.

(d) Samples of the milled lactose particles were mixed with the active particles. 0.4 g of salbutamol sulphate (mass median diameter 4.6 μm) were added to 50 g of the milled lactose particles in a plastics container. After blending for ten minutes using an Erweka AR400 cube blender, the mixture was removed from the container and screened through a sieve of mesh aperture diameter 250 μm to remove any large agglomerations of active particles which may have formed. The mixture was returned to the container and blended for a further twenty minutes. The mixture was stored in the plastics container for five days to allow the decay of any accumulated electric charges.

The blending process was repeated for a 50 g sample of lactose particles which had been taken from the sieved sample of particles of diameter between 90 μm and 125 μm, but which had not been milled, to give a comparative example.

(e) After five days, six samples each of 100 mg of mixture were taken from the container containing the milled carrier particles, and four samples each of 100 mg were taken from the container containing the unmilled carrier particles. Each sample was used to fill a respective one of ten size three capsules (size 3 opaque, Elanco BN 3D056D). Those capsules were allowed to stand for two days to allow the decay of any accumulated electric charge.

(f) In order to assess the effectiveness of the mixing method, ten 100 mg samples were taken randomly from each of the two mixes (and were made up to 250 ml with distilled water) and were analyzed using spectrofluorimetry on a Shimadzu RS S40 spectrofluorimeter at an excitation wavelength of 223 nm and an emission wavelength of 303 nm as described below. The samples were analyzed against standard solutions of 1 µg/ml salbutamol sulphate and 5 µg/ml salbutamol sulphate, and the concentrations of each of the samples were calculated.

The mass of salbutamol in the mix could therefore be calculated for each of the samples. The coefficient of variation (CV: calculated as the standard deviation of the values divided by the mean value×100) of the mass was calculated for the ten samples of the mixture containing the milled particles and for the ten samples of the mixture containing the unmilled particles.

Any mixture for which the value for the coefficient of variation is calculated to be lower than 4.0 is usually regarded as being a homogeneous mixture. The mixture containing the unmilled particles gave a CV of 0.7 and the mixture containing the milled particles gave a CV of 1.3. Thus both mixtures were considered to be homogeneous.

(g) The effect of the milling method on the surfaces of the lactose particles was verified using a dry powder inhaler device and a pharmacopoeial apparatus, for in vitro assessment of inhaler performance.

Figure 1A:
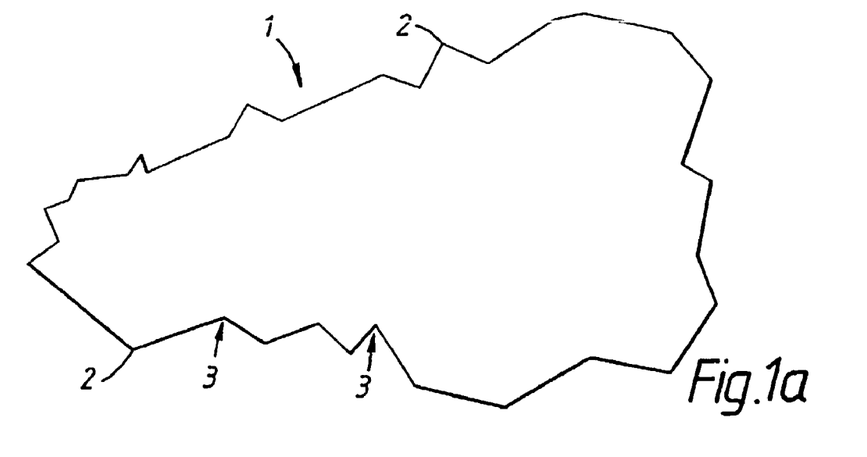
Figure 1B:
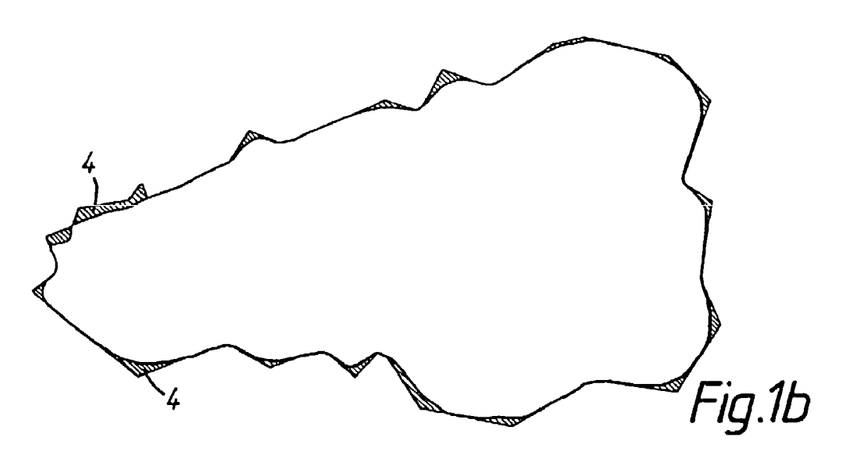
Figure 1C:
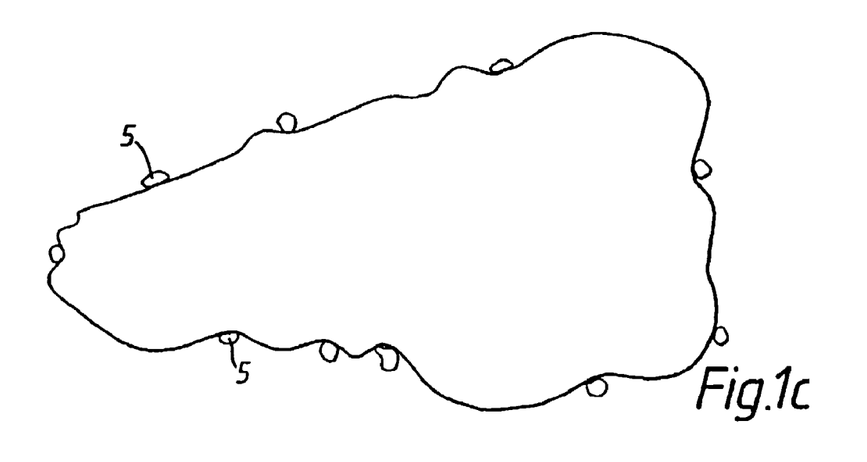
Figure 2:
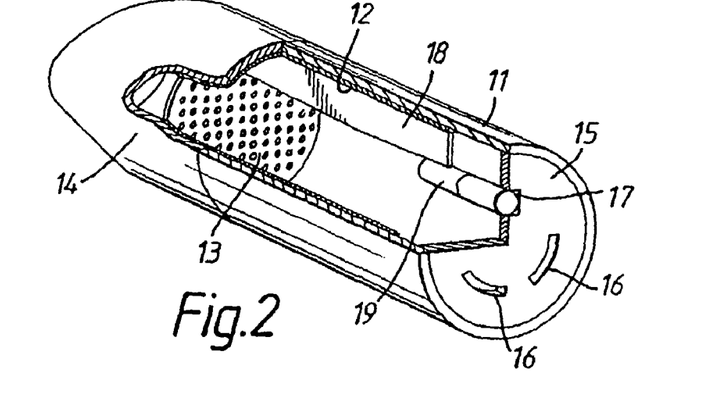

(g) (i) FIG. 2 shows a view of a dry powder inhaler known as a Rotahaler. The inhaler comprises an outer cylindrical barrel 11 and an inner cylindrical barrel 12 of similar radius such that the inner barrel 12 is just able to fit inside the outer barrel 11. A mesh 13 is attached across an end of the inner barrel 12 and a mouthpiece 14 is attached around that end section of the inner barrel 12. The outer barrel 11 is closed at one end by an end section 15 which contains inlet slots 16 and an aperture 17. The inner barrel 12 also contains a fin 18 along a length of the inner barrel at the open end, the fin extending radially inwards from the internal surface of the inner barrel 12.

To operate the device, the inner barrel 12 is inserted into the open end of the outer barrel 11 such that the mouthpiece meets the outer barrel 11 and the open end of the inner barrel is at the end section 15. Capsule 19 containing the mixture of carrier particles and active particles is inserted into the aperture 17 such that a portion of the capsule 19 is held in the end section 15, and a portion of the capsule 19 extends into the inner barrel 12. The outer barrel 11 is rotated relative to the inner barrel 12 and thus the fin 18 engages and breaks the capsule. A patient inhales through the mouthpiece 14, air is drawn into the Rotahaler through the inlet slots 16, and the contents of the capsule are discharged into the inner barrel as a cloud of powder and inhaled via the mouthpiece 14. The mesh 13 prevents the inhalation of large particles or of the broken capsule.

Figure 3:
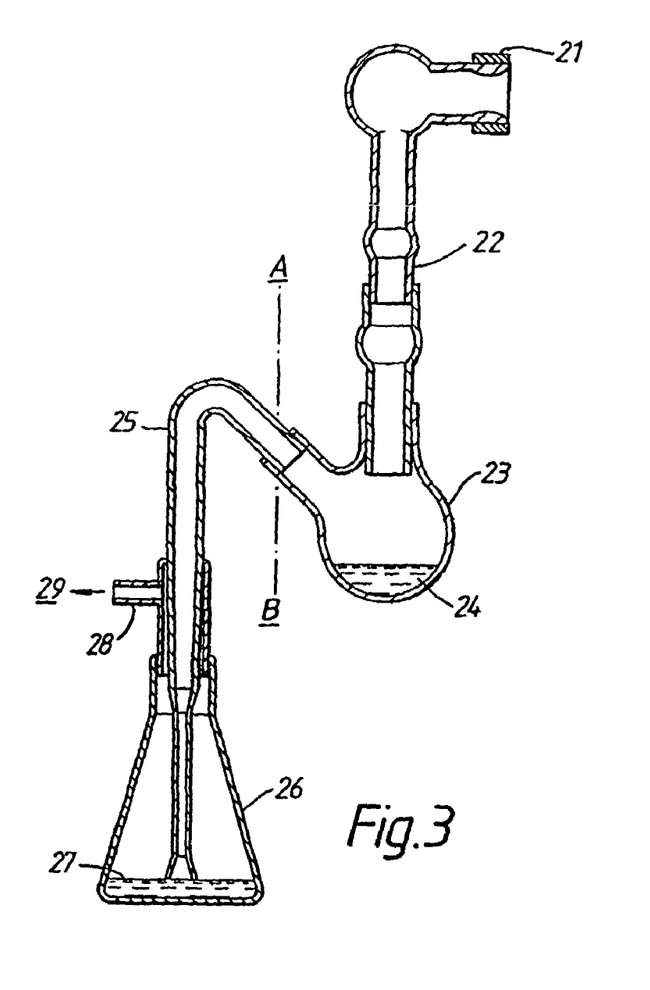

(g) (ii) FIG. 3 shows a diagrammatic arrangement of a twin stage impinger (TSI). The TSI is a two stage separation device used in the assessment of oral inhalation devices. Stage one of the apparatus is shown to the right of the line AB in FIG. 3 and is a simulation of the upper respiratory tract. To the left of that line is stage two which is a simulation of the lower respiratory tract.

The TSI comprises a mouth 21 which comprises a polydimethylsiloxane adaptor, moulded to accept the mouthpiece of the inhaler device, upper tubing 22 and upper impinger 23 to simulate the upper respiratory tract, the upper impinger containing liquid 24, and lower tubing 25 and lower impinger 26 to simulate the lower respiratory tract, the lower impinger containing liquid 27. The lower impinger 26 is connected via an outlet pipe 28 to a pump 29 which draws air through the TSI apparatus at a predetermined rate. The base of the lower tubing 25 is at the level of the liquid 27 such that all the air drawn through the TSI bubbles through the lower liquid 27. The liquid used in both the upper and lower impinger is distilled water.

In use, the inhaler is placed in a mouth 21 of the TSI. Air is caused to flow through the apparatus by means of a pump 29 which is connected to stage two of the TSI. Air is sucked through the apparatus from the mouth 21, flows through upper tubing 22 via the upper impinger 23 and the lower tubing 25 to the lower impinger 26 where it bubbles through liquid 27 and exits the apparatus via outlet pipe 28. The liquid 24 in the upper impinger 23 traps any particle with a size such that it is unable to reach stage two of the TSI. Fine particles, which are the particles able to penetrate to the lungs in the respiratory tract, are able to pass into stage two of the TSI where they flow into the lower impinger liquid 27.

(h) 30 ml of distilled water was put into the lower impinger 26 and 7 ml of distilled water was put into the upper impinger 23. The lower tubing 25 was arranged such that its lower end was at the level of the water in the lower impinger 26. The pump 29 was adjusted to give an air flow rate of 60 litres per minute in the apparatus.

The Rotahaler was weighed when empty. One of the prepared capsules was inserted into aperture 17 and the inhaler was reweighed. The mouthpiece 14 of the inhaler was connected to the mouth 21 of the TSI, the outer barrel 11 was rotated to break the capsule 19 and the pump was switched on and timed for a period of ten seconds. The pump was then switched off and the Rotahaler was removed from the TSI, reweighed and the amount of powder lost from the inhaler calculated.

The remaining powder in the inhaler was washed into a flask for analysis and made up to 100 ml with distilled water. The sections of the apparatus making up stage one of the TSI were washed into a second flask and made up to 250 ml with distilled water. The sections making up the second stage of the TSI were washed into a third flask and made up to 100 ml with distilled water.

The other capsules were tested in the same way in a predetermined random order.

The contents of the flasks were then analyzed spectrofluorimetrically using a Shimadzu R5 S40 spectrophotofluorimeter at excitation wavelength 223 nm and emission wavelength 303 nm. Standard solutions of the active particles were also analyzed thus enabling the amount of active particles deposited in each of the stages to be determined. Salbutamol gives good fluorescence.

(j) The contents of the flasks containing the washing from the stages of the TSI were analyzed using the spectrophotofluorimeter at excitation wavelength 223 nm and emission wavelength of 303 nm. The scan speed was set at medium and sensitivity high with an excitation slit width of 10 nm and emission slit width of 10 nm. The relative emission intensities were measured for each of the salbutamol solutions.

Standard solutions containing 1 μg/ml and 5 μg/ml of salbutamol sulphate were made up using distilled water and the spectrofluorimetric analysis was repeated for each of those two samples.

Assuming a linear relationship between the intensity of the emitted fluorescence and the concentration of salbutamol in the samples, the concentration of salbutamol in the samples taken from the TSI could be calculated via the known intensities and concentrations of the standard samples.

The percentage of salbutamol in each stage of the TSI could be calculated for each capsule and the mean for the milled samples and the unmilled samples could be calculated.

(k) Table 1 below shows the relative intensity (RI) measured spectrofluorimetrically for the samples taken from each of the stages of the TSI: the inhaler device (R), stage 1 (1) and stage 2 (2). From those RI values, the percentage of active ingredient, released from the capsule, that was present in each stage of the TSI could be calculated for each of the unmilled samples A1 to A4 and the milled samples B1 to B6.

Table 2 shows the mean percentage of active ingredient in each stage, calculated for the six milled samples and the four unmilled samples.

From the value of the mass of the capsule, the mass of the Rotahaler, and the mass of the Rotahaler and capsule after the powder had been expelled, the mass of powder lost from the inhaler can be calculated. Thus the mass of the active ingredient lost ran be calculated, assuming the mixture is homogenous.

From the RI values for the standard solutions of salbutamol of known concentration, the concentration of salbutamol and hence the amount of salbutamol in each of stage 1 and stage 2 was calculated for each capsule. This amount is expressed in Table 3 as the mean percentage lost from the inhaler for the milled and unmilled samples.

TABLE 1

| Sample | R I (R, 1, 2) | % of expelled salbutamol (R, 1, 2) |
|---|---|---|
| B1 | 26.4, 12.3, 19.2 | 36.24, 38.20, 25.55 |
| B2 | 52.8, 5.7, 6.4 | 37.68, 14.27, 6.76 |
| A1 | 26.3, 20.6, 9.8 | 30.97, 59.13, 9.89 |
| B3 | 38.9, 9.2, 15.4 | 54.76, 25.90, 19.33 |
| A2 | 24.7, 20.3, 8.8 | 31.01, 60.53, 6.50 |
| A3 | 46.5, 11.5, 6.3 | 61.41, 32.71, 5.86 |
| B4 | 13.8, 6.3, 9.3 | 39.59, 35.96, 24.45 |
| B5 | 56.8, 3.1, 3.8 | 92.45, 4.54, 3.00 |
| A4 | 19.6, 21.6, 8.0 | 22.4, 62.38, 15.23 |
| B6 | 47.8, 7.3, 9.1 | 69.31, 19.97, 10.73 |

TABLE 2

|  | A (unmilled) | B (milled) |
|---|---|---|
| in the inhaler device | 43.8 | 45.5 |
| in stage one | 53.7 | 32.8 |
| in stage two | 9.4 | 17.4 |

TABLE 3

|  | A (unmilled) | B (milled) |
|---|---|---|
| in stage one | 83.4 | 61.6 |
| in stage two | 16.6 | 38.4 |

The results show that there has been a significant increase in the deposition Of the active particles in stage two of the apparatus for the lactose which has had the ball milling treatment. An increased percentage of active particles delivered to the second stage of the TSI corresponds to increased deposition in the lower respiratory tract. Thus the treatment has been successful and the surfaces of the lactose carrier particles have been modified by the milling process such that the active particles adhere less strongly to the lactose carrier particles.

EXAMPLE 2

Carrier particles were prepared by the following method. Meggle lactose EP D30 (as described for Example 1 above) was used.

(a) The lactose was sieved by the following method to give samples having particles with a range of diameter from 63 to 90 μm. Successive samples of 50 g of lactose were sieved mechanically for 40 minutes using a stack of woven wire stainless steel sieves of mesh diameters 63 μm, 90 μm, 125 μm, 180 μm and 250 μm. The sieving process corresponded to that described in Example 1(a).

200 g samples of the lactose were taken from the particles that had passed through the 90 μm mesh sieve, but had remained on the 63 μm sieve. Those particles could be considered to have a diameter between 63 μm and 90 μm.

(b) The samples obtained in step (a) above were milled in a porcelain ball mill (manufactured by Pascal Engineering Company). 400 ml of plastics grinding balls having an approximate diameter of 20 mm were used and the mill was revolved at 6 revolutions per minute for six hours.

(c) Samples of the milled lactose particles obtained in step (b) were mixed with active particles. 0.132 g of beclomethasone dipropionate (BDP) (mass median diameter 1.13 μm) were added to 29.87 g of the milled lactose particles in a glass mortar. Each 30 g of mixture was blended in the mortar using a glass pestle.

The blending process with 0.264 g of BDP was repeated for a 29.74 g sample of lactose particles having a diameter between 63 and 90 μm, but which had not been milled, to give a comparative example.

(d) After one day, several samples each of 25 mg of mixture were taken from the container containing the unmilled particles and from the container containing the milled particles. Each sample was used to fill a respective one of size three capsules (size 3 transparent capsules obtained from Davcaps of Hitchen, Herts., England). Those capsules were allowed to stand for one day to allow the decay of any accumulated electric charge.

(e) The effect of the milling method on the surfaces of the lactose particles was verified using a dry powder inhaler device and a pharmacopoeial apparatus as described in steps (g) and (h) of Example 1 above, the contents of the flasks containing the washing from the stages of the TSI being assayed using High Performance Liquid Chromotography (HPLC) analysis for the content of BDP and compared against standard solutions containing 0.5 μg/ml and 1 g/ml of BDP.

The percentage of BDP in each stage of TSI was calculated from the standard response for each capsule and the mean for the milled samples and the unmilled samples could be calculated.

(f) Table 4 below shows the BDP content (in μg) recovered from each stage of the TSI as an average for the samples of the milled and the unmilled material. The respirable fraction (calculated as the percentage of the total amount of drug emitted from the device, that reaches stage two of the TSI) gives an indication of the proportion of active particles which would reach the deep lung in a patient. The numbers in brackets indicate the coefficient of variation for each value.

TABLE 4

| | unmilled | milled |
|---|---|---|
| Device | 31.8 (23.0) | 19.3 (17.2) |
| Stage 1 | 164.4 (5.8) | 78.6 (7.1) |
| Stage 2 | 5.9 (14.2) | 5.8 (15.9) |
| Respirable Fraction (%) | 3.5 (11.6) | 6.9 (12.5) |

The results show that there has been an increase in the deposition of active particles in Stage two of the TSI: indicating an increased deposition in the deep lung for the milled samples.

EXAMPLE 3

Carrier particles were prepared by the following method:

(a) Samples of 200 g Meggle lactose EP D30 were sieved mechanically for 10 minutes using a single large (60 cm diameter) screen vibrated on a rotary shaking device (William Boulton Ltd.). The lactose was sieved first on a 125 μm mesh, then subsequently on 90 μm and finally a 63 μm mesh to obtain the same size separation obtained in step (a) of Example 2 above.

(b) The samples obtained in step (a) above were milled in a porcelain ball mill (Pascal Engineering company). 1200 ml of plastics grinding balls having an approximate diameter of 20 mm were used and the mill was revolved at 6 revolutions per minute for 24 hours.

(c) Samples of the milled lactose particles obtained in step (b) were mixed with active particles. 0.3182 g salbutamol sulphate (mass median diameter 1.97 μm) were added to 29.68 g of the milled lactose particles and mixed in a Turbula mixer (type TZC, WAB AG, Switzerland) for 30 minutes.

(d) After one day, several samples each of 25 mg of mixture were taken from the container containing the milled carrier particles, and several samples each of 25 mg were taken from the container containing the unmilled carrier particles. Each sample was used to fill a respective one of size three capsules (transparent capsules obtained from Davcaps). Those capsules were allowed to stand for one day to allow the decay of any accumulated electric charge.

(e) The effect of the milling method on the surfaces of the lactose particles was verified using a dry powder inhaler device and a pharmacopoeial apparatus as described in steps (g) to (j) of Example 1 above, the contents of the flasks containing the washing from the stages of the TSI being arranged using HPLC analysis as in Example 2.

(f) Table 5 below shows the salbutamol content (in μg) recovered from each stage of the TSI as an average for the samples of the milled and the unmilled material. The respirable fraction (defined in Example 2(f) above) was calculated. The numbers in brackets indicate the coefficient of variation for each value.

TABLE 5

| | unmilled | milled |
|---|---|---|
| Device | 32.4 (5.3) | 61.3 (8.8) |
| Stage 1 | 144.1 (5.1) | 116.6 (10.7) |
| Stage 2 | 12.2 (14.3) | 25.2 (10.2) |
| Respirable Fraction (%) | 7.8 (10.8) | 17.9 (14.1) |

The results show that there has been an increase in the deposition of active particles in stage two of the TSI, indicating an increased deposition in the lower lung, for the milled samples.

EXAMPLE 4

Carrier particles were prepared by the following method.

(a) 50 g samples of milled and unmilled Meggle lactose EP D30 particles were prepared as described in steps (a) and (b) in Example 2 except that the mill was operated at 60 rpm for 6 hours using 90 to 125 μm lactose starting material.

(b) 200 g samples of Meggle lactose EP D30 particles re milled in a porcelain ball mill using plastics grinding balls. The mill was revolved at 60 rpm for 24 hours. The milling fractured the lactose particles. Agglomerates of fine lactose particles having particle size in the range of from 0.5 to 90 μm were produced, the median diameter being 24 μm.

(c) 2 g of particles produced in step (b) were mixed with 18 g of milled particles produced in step (a).

(d) The process described in Example 2(c) and (d) was carried out for the milled and treated and the unmilled lactose samples.

(e) The effect of the treatment method on the surfaces of the lactose particles was verified as described in steps (g) and (h) of Example 1 except that the samples were assayed for drug content using HPLC analysis as in Example 2.

(f) The respirable fraction calculated in respect of the treated sample was 25.5%.

The invention claimed is:

1. A method of producing particles for use as carrier particles in dry powder inhalers, the method comprising the steps of:

selecting particles of a pharmacologically inert material or combination of materials, to obtain carrier particles having a diameter of between 50 μm and 1000 μm;

milling the selected carrier particles to dislodge small grains from the surfaces of the selected particles without substantially changing the size of the selected carrier particles, wherein the step of selecting the size of the carrier particles occurs prior to the step of milling the selected particles; wherein the milling step is performed in a recirculated low fluid energy mill, and wherein the small grains become reattached to the surfaces of the carrier particles.

2. A method according to claim 1 wherein the particles are crystalline sugar particles.

3. A method according to claim 1 wherein the particles are lactose particles.

4. A method of producing a dry powder for use in dry powder inhalers, the method including producing carrier particles using a method according to claim 1, and mixing the carrier particles with active particles such that the active particles adhere to the surfaces of carrier particles.

5. A method according to claim 4 wherein the diameter of the active particles is between 0.1 μm and 3 μm.

6. A method according to claim 4 wherein the carrier particles and the active particles are mixed in a container made from a plastics material.

7. A method according to claim 4 wherein the carrier particles and the active particles are mixed for at least five minutes.

8. A method according to claim 7 wherein the carrier particles and the active particles are mixed for thirty minutes.

9. A method according to claim 7 wherein the mixing is interrupted and the mixture of carrier particles and active particles is sieved.

10. A method according to claim 9 wherein sieve mesh size is about 250 μm.

11. A method according to claim 4 wherein the carrier particles and the active particles are mixed in a ratio by weight of 125 to 1.

12. A method according to claim 4 wherein the active particles include a $\beta_2$-agonist.

13. A method according to claim 12 wherein the active particles include terbutaline, a salt of terbutaline or a combination thereof.

14. A method according to claim 12 wherein the active particles include salbutamol, a salt of salbutamol or a combination thereof.

15. A method according to claim 14 wherein the active particles include salbutamol sulphate.

16. A method as claimed in claim 4, wherein the small grains become reattached to the surface of the carrier particles.

17. A method as claimed in claim 1, wherein the small grains become reattached to the surface of the carrier particles in a mixing step that follows the milling step.

18. A method according to claim 3, wherein diameter of the selected particles is less than 355 μm.

19. A method according to claim 3, wherein diameter of the selected particles lies between 60 μm and 250 μm.

20. A method according to claim 3, wherein diameter of the selected particles lies between 90 μm and 250 μm.

* * * * *